United States Patent [19]

Lindauer et al.

[11] Patent Number: 5,234,689

[45] Date of Patent: Aug. 10, 1993

[54] MULTI-PURPOSE FRAGRANCE COMPOSITION

[75] Inventors: Jerome I. Lindauer, Hillsdale, N.J.; Marcia Edwards, Brooklyn, N.Y.

[73] Assignee: La Parfumerie, Inc., New York, N.Y.

[21] Appl. No.: 824,708

[22] Filed: Jan. 21, 1992

Related U.S. Application Data

[63] Continuation of Ser. No. 610,508, Nov. 8, 1990, abandoned.

[51] Int. Cl.$^5$ .......................... A61K 7/46; A61K 7/50; A61K 9/107
[52] U.S. Cl. .................. 424/401; 424/78.03; 252/DIG. 5; 514/938; 514/939; 514/943
[58] Field of Search ................... 424/401, 70; 252/DIG. 5; 514/938, 939, 943

[56] References Cited

U.S. PATENT DOCUMENTS 3,939,260  2/1976  Lafon .................................. 424/401

Primary Examiner—Thurman K. Page
Assistant Examiner—Raj Bawa
Attorney, Agent, or Firm—Woodcock Washburn Kurtz Mackiewicz & Norris

[57] ABSTRACT

A multi-purpose, clear, anhydrous, liquid perfume composition comprising effective amounts of each of (a) one or more skin protective agents, (b) one or more skin moisturizers or emollients, (c) one or more emulsifiers, and (d) one or more perfume oils is disclosed. This composition can be used directly on the skin as a perfume, e.g., in the form of a vehicle similar to a dry oil spray, can be added directly to bath water as a perfumed bath oil, or can be mixed with water, e.g., in a jar, bottle or in situ on wet skin, to produce an emulsion body lotion.

10 Claims, No Drawings

MULTI-PURPOSE FRAGRANCE COMPOSITION

This is a continuation of application Ser. No. 610,508, filed Nov. 8, 1990, now abandoned.

BACKGROUND OF THE INVENTION

This invention relates to a fragrance composition which can be used as a dry oil spray, a bath oil, or, when mixed with water, as a skin moisturizing/protecting composition.

The desirability of applying perfumes to the skin is self-evident, as indicated by the millions of dollars spent each year by consumers for fragrance products of various types. The majority of products which have been created and commercialized for the purpose of applying aromatic perfume oils to the skin have comprised combinations of alcohol, water and perfume oil. However, there also exist on the market products that contain no alcohol or water, known as dry oil sprays. Dry oil sprays are preferred by some consumers because alcohol can tend to create or exacerbate dry skin conditions. In addition, these products can act as moisturizers for the skin by slowing down transepidermal water loss.

There are also products on the market that can be added to a bath water for the purpose of moisturizing or providing emolliency to the skin. These products generally contain a fragrance and are commonly known as bath oils. Many commercial bath oils cause the phenomenon known as "bath tub ring", resulting when insoluble calcium soaps combine with the bath oil droplets and adhere to the sides of the bath tub.

Finally, there are many body lotions or creams on the market. These products are generally emulsions, have moisturizing and emolliency properties and may be applied directly to the skin.

Until now, there has been no single product available which could be used not only as a dry oil spray, but also as a bath oil and as a body lotion by the consumer. The desirability of such a multi-purpose product is clear as its availability would allow a consumer to make a single purchase and obtain a product with properties that could previously be obtained only by purchasing several products.

SUMMARY OF THE INVENTION

This invention relates to a multi-purpose, clear, substantially anhydrous, liquid perfume composition and comprises effective amounts of each of (a) one or more skin protective agents, (b) one or more skin moisturizers or emollients, (c) one or more emulsifiers, and (d) one or more perfume oils. This composition can be used directly on the skin as a perfume, e.g., in the form of a vehicle similar to a dry oil spray, can be added directly to bath water as a perfumed bath oil, or can be mixed with water, e.g., in a jar, bottle or in situ on wet skin, to produce an emulsion body lotion.

DETAILED DESCRIPTION OF THE INVENTION

The compositions of this invention contain one or more skin protective agents. These agents are well known in the art and protect the skin by forming an occlusive film which helps to retain moisture in or on the surface of the skin. The preferred skin protective agents are silicone and silicone derivatives such as, but not limited to, dimethicone, cyclomethicone and silicone copolymers.

The compositions of this invention also contain one or more moisturizers or emollients. As with the skin protective agents, suitable moisturizers and emollients are well known in the art. Examples of suitable such agents include, but are not limited to, mineral oil, saturated hydrocarbons, fatty acid esters, triglycerides, vegetable oils and glycerine soaps. Specific examples include PPG-2 myristyl ether proprionate, caprylic/capric triglyceride, squalane, isostearyl neopentanoate, glyceryl oleate, and safflower oil.

The compositions of this invention also contain one or more emulsifiers. Such compounds generally are materials having a lipophilic group and a hydrophilic group. For the purpose of the compositions of this invention, emulsifiers having a hydrophilic/lipophilic balance (HLB) in the range of about 3 to 12 are preferred. Examples of suitable such emulsifiers include, but are not limited to, glyceryl oleate, triethanolamine stearate, sorbitan monooleate and polyoxyethylene sorbitan monooleate.

Finally, the compositions of this invention contain one or more perfume oils. The perfume oils are present in the composition in an amount effective to provide the composition with the desired fragrance and preferably comprise about 1 to 50 weight % of the total weight of the composition, more preferably about 1 to 20 weight %. The skin protective agents are present in the composition in an amount effective to provide the composition with skin protective properties and preferably comprise about 1 to 80 weight %, more preferably about 50 to 70 weight % of the total composition. The moisturizers and/or emollients are also present in an amount effective to provide the composition with the desired moisturizing properties and preferably comprise about to 80 weight %, more preferably about 15 to 25 weight %, of the total composition. Finally, the emulsifier(s) are present in an amount effective to help the composition mix with water to form a creamy oil in water emulsion which can be used as a skin or body lotion. Generally, then, the emulsifier(s) comprise about 2 to 12 weight %, more preferably about 4 to 8 weight % of the total composition.

The multi-purpose fragrance composition of this invention may also contain additional ingredients such as but not limited to dyes or colorants, preservatives such as anti-oxidants to enhance shelf life, and antibacterial agents.

The claimed fragrance composition is substantially anhydrous and appears to the naked eye as a clear liquid. When the composition is mixed with water, for example, either in a container or upon application to wet skin, the substantially clear, oily liquid is converted to a milky or creamy lotion suitable for use as a body or skin lotion. It will be appreciated that it might be possible to add very small amounts of water to the composition without changing its appearance as a clear liquid. Thus, the term "substantially anhydrous" is used not to exclude the possibility of the presence of any water in the composition, but to exclude the presence of an amount of water sufficient to alter the appearance of the product as a clear liquid. Generally, to form a body lotion, the claimed composition is mixed with water in a range of from about 1:1 parts composition/water to 1:9 parts composition/water, although these ranges are not critical.

The following example is provided to illustrate the claimed compositions, but is not intended to limit the scope of the invention.

EXAMPLE

A preferred multi-purpose fragrance composition of this invention was prepared by combining the following components:

| Component | % By Weight |
| --- | --- |
| Cyclomethicone (Dow Corning Silicone 344 Fluid) | 62.8 |
| PPG-2 Myristyl Ether Proprionate ("Crodamol PMP", Croda Chemicals) | 5.0 |
| Caprylic/Capric Triglyceride ("Neobee M-5", Stepan Chemicals) | 2.0 |
| Squalane ("Robane", Robeco Chemicals) | 1.7 |
| Isostearyl Neopentanoate ("Ceraphyl 375", Van Dyk Chemicals) | 1.3 |
| Glyceryl Monoleate (Stepan Chemicals) | 1.3 |
| Glyceryl Oleate and Propylene Glycol ("Arlacel 186", Imperial Chemical Ind.) | 6.0 |
| Edible Safflower Oil | 2.5 |
| Propyl Parben | 0.3 |
| Butylated Hydroxyanisol (BHA) | 0.1 |
| Perfume Oil | 5.0 |
|  | 100.00 |

As can be seen from this example, it may be desirable, to obtain a product with the desired "feel", to combine a number of different moisturizing agents and emollients. In this particular example, a desirable product was obtained by utilizing a combination of agents of one or more vegetable oils and one or more saturated hydrocarbons.

Although the composition set forth above is the preferred embodiment of the invention, other suitable compositions may be made using the same components in the following different weight percentage ranges:

| Component | % By Weight |
| --- | --- |
| Cyclomethicone (Dow Corning Silicone 344 Fluid) | 1–80 |
| PPG-2 Myristyl Ether Proprionate ("Crodamol PMP", Croda Chemicals) | 1–80 |
| Caprylic/Capric Triglyceride ("Neobee M-5", Stepan Chemicals) | 1–25 |
| Squalane ("Robane", Robeco Chemicals) | 0.2–10 |
| Isostearyl Neopentanoate ("Ceraphyl 375", Van Dyk Chemicals) | 1–80 |
| Glyceryl Monoleate (Stepan Chemicals) | 1–10 |
| Glyceryl Oleate and Propylene Glycol ("Arlacel 186", Imperial Chemical Ind.) | 1–10 |
| Edible Safflower Oil | 1–10 |
| Propyl Parben | 0.05–0.20 |
| Butylated Hydroxyanisol (BHA) | 0.02–0.50 |
| Perfume Oil | 1–20 |

We claim:

1. A multi-purpose, clear, anhydrous, liquid fragrance composition which can be used as a dry oil spray, a bath oil or as a body lotion by the consumer, consisting essentially of:
   (a) about 1 to 80 weight percent one or more silicone based skin protective agents;
   (b) about 1 to 80 weight percent one or more skin moisturizers or emollients selected from mineral oil, saturated hydrocarbons, fatty acid esters, triglycerides, vegetable oils and glycerine soaps;
   (c) about 4 to 8 weight percent one or more emulsifiers having a hydrophilic/liphilic balance (HLB) in the range of about 3 to 12, and;
   (d) about 1 to 50 weight percent one or more perfume oils, said composition being usable as a dry oil spray in the anhydrous state, or usable as a body lotion or bath oil by mixing said composition with suitable amount of water.

2. The multi-purpose perfume composition of claim 1 where said silicone selected from the group consisting of dimethicone and cyclomethicone.

3. A multi-purpose perfume composition of claim 2 wherein said skin protective agent comprises cyclomethicone.

4. The multi-purpose perfume composition of claim 1 where said emulsifiers are selected from the group consisting of glyceryl oleate, triethanolamine stearate, sorbitan monooleate and polyoxyethylene sorbitan monooleate.

5. The multi-purpose perfume composition of claim 4 where said emulsifier comprises glyceryl oleate.

6. The multi-purpose perfume composition of claim 1 which further comprises additives selected from the group consisting of coloring agents, anti-oxidants and anti-bacterial agents.

7. A multi-purpose perfume composition of claim 1 wherein said one or more skin protective agents comprise cyclomethicone, said one or more moisturizers and emollients comprise a combination of one or more triglycerides, one or more fatty acid esters and one or more vegetable oils, and said one or more emulsifiers have an HLB in the range of about 3 to about 12.

8. The multi-purpose perfume composition of claim 7 wherein said emulsifiers are selected from the group consisting of glyceryl oleate, triethanolamine stearate, sorbitan monooleate and polyoxyethylene sorbitan monooleate.

9. A method of moisturizing the skin with a perfume moisturizing composition such as a body lotion or bath oil, comprising:
   providing a multi-purpose, clear, anhydrous, liquid fragrance composition which consists essentially of:
   (a) about 1 to 80 weight percent one or more silicone based skin protective agents;
   (b) about 1 to 80 weight percent one or more skin moisturizers or emollients selected from mineral oil saturated hydrocarbons, fatty acid esters, triglycerides, vegetable oil and glyceride soaps;
   (c) about 4 to 8 weight percent one or more emulsifiers having a hydrophilic/liphilic balance (HLB) in the range of about 3 to 12, and;
   (d) about 1 to 50 weight percent one or more perfume oils; and
   adding water to said composition to create a body lotion or bath oil, whereby the same composition can be used as a dry oil spray, a body lotion or a bath oil.

10. A method according to claim 9, wherein said water is added in an amount within the range from about equal parts composition: water to about one part composition: nine parts water.

* * * * *